United States Patent [19]

Nevill et al.

[11] Patent Number: 4,940,720

[45] Date of Patent: Jul. 10, 1990

[54] MICROBICIDAL COMPOSITIONS

[75] Inventors: David J. Nevill, Riehen; Bernhard Steck, Muntelier, both of Switzerland

[73] Assignee: Ciba-Geigy Corporation, Ardsley, N.Y.

[21] Appl. No.: 388,782

[22] Filed: Aug. 2, 1989

[51] Int. Cl.⁵ .................... A01N 43/36; A01N 43/64
[52] U.S. Cl. .................................... 514/383; 514/427
[58] Field of Search ............................... 514/383, 427

[56] References Cited

FOREIGN PATENT DOCUMENTS 0126430  5/1984  European Pat. Off. .
0236272  9/1987  European Pat. Off. .
2024824  1/1980  United Kingdom .

*Primary Examiner*—Allen J. Robinson
*Attorney, Agent, or Firm*—George R. Dohmann

[57] ABSTRACT

The combination of the plant microbicide 3-cyano-4-(2,3-dichlorophenyl)-pyrrole ("fenpiclonil") with the plant microbicide 1-(1H-1,2,4-triazol-1-yl)-2-methoxy-2-[4-(4-chlorophenoxy)-2-chlorophenyl]-butane results in a synergistically enhanced activity in the control of plant diseases. Plant microbicidal compositions based on such combinations are especially suitable for treating seed.

4 Claims, No Drawings

MICROBICIDAL COMPOSITIONS

The present invention relates to microbicidal mixtures having synergistically enhanced activity against plant diseases and to methods of using such mixtures, especially for dressing seed.

The invention relates especially to the control or prevention of diseases in cereal cultivation.

It has been found that a combination of the active ingredient component I), 3-cyano-4-(2,3-dichlorophenyl)-pyrrole ("fenpiclonil") of formula I

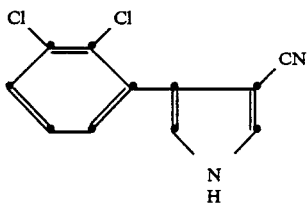

with the active ingredient component II), 1-(1H-1,2,4-triazol-1-yl)-2-methoxy-2-[4-(4-chlorophenoxy)-2-chlorophenyl]-butane of formula II

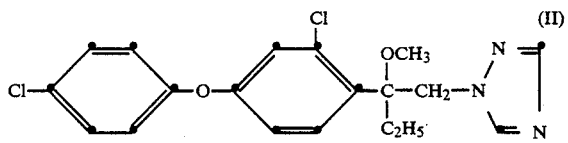

or with a salt thereof results in a synergistically enhanced activity in the control and prevention of plant diseases.

The compound of formula I is mentioned in DE-OS 2,927,480 (or in GB Patent Application 2,024,824) among other intermediates. Its use as a fungicidal active ingredient is described in EP-A 236272. It is distinguished especially as a contact fungicide.

The compound of formula II is described as a fungicidal active ingredient in European Patent Application 126 430. The action of that triazole derivative is based on the inhibition of ergosterol biosynthesis.

The mentioned salts of the compound of formula II can be prepared by reacting the base with acids.

Of the acids that may be used for the preparation of salts of formula II there may be mentioned: hydrohalic acid, such as hydrofluoric acid, hydrochloric acid, hydrobromic acid or hydriodic acid and sulfuric acid, phosphoric acid, nitric acid and organic acids, such as acetic acid, trifluoroacetic acid, trichloroacetic acid, propionic acid, glycolic acid, thiocyanic acid, lactic acid, succinic acid, citric acid, benzoic acid, cinnamic acid, oxalic acid, formic acid, benzenesulfonic acid, p-toluenesulfonic acid, methanesulfonic acid, salicylic acid, p-aminosalicylic acid, 2-phenoxybenzoic acid, 2-acetoxybenzoic acid or 1,2-naphthalenedisulfonic acid.

The term "salts" also includes metal complexes of the basic component II. Those complexes consist of the fundamental organic molecule and an inorganic or organic metal salt, for example the halides, nitrates, sulfates, phosphates, acetates, trifluroracetates, trichloroacetates, propionates, tartrates, sulfonates, salicylates, benzoates, etc. of elements of the second main group, such as calcium and magnesium, and of the third and fourth main groups, such as aluminum, tin or lead, and of the first to eighth sub-groups, such as chromium, manganese, iron, cobalt, nickel, copper, zinc, etc. The sub-group elements of the 4th period are preferred. The metals may be present in any of the various valencies attributed to them. The metal complexes may be mono- or poly-nuclear, that is to say they may contain one or more organic molecular components as ligands.

It is known to the person skilled in the art that the activity of a fungicidal active ingredient can be greatly enhanced or broadened by the addition of another fungicide having a different spectrum of activity.

It has surprisingly been found, however, that the combination of the active ingredients I and II results in a quite unexpectedly substantial enhancement of activity against seed-borne and soil-borne fungi. The enhancement of activity achieved by the combination according to the invention is far greater than the activity that would be expected from the addition of the activities of the two individual components, that is to say, the combination has synergistic activity.

Apart from synergistic fungicidal activity, the mixtures according to the invention exhibit a pronounced plant growth promoting activity which depends on the composition of the mixture according to the invention to approximately the same extent as does the fungicidal activity. Accordingly, the plant growth promoting activity of the mixture according to the invention can also be regarded as synergistic.

The present invention therefore permits the dressing of seeds with lower amounts of biocides than known hitherto and therefore constitutes a very substantial enrichment of the state of the art.

The present invention relates not only to the application of mixtures of components I and II to seed but also to the application of the individual pure components in immediate succession.

Favourable ratios of the two active ingredients are I:II = 20:1 to 1:20, especially I:II = 10:1 to 1:10 and very especially I:II = 5:1 to 1:5. Other advantageous ratios are I:II = 2:1 to 1:2 or 5:2 to 2:3 or 3:2 to 1:1.

An enhanced activity is also observed when the compound of formula I is combined with other active ingredients, provided the latter are inhibitors of demethylation by the ergosterol synthesis route of fungi. Such demethylation inhibitors are bitertanol, diniconazole, ethyltrianol, flutriafol, flusilazole, furconazole, imazalil, myclobutanil, cyproconazole, triadimefon, triadimenol and others, whose structure and fungicidal activity are known to the person skilled in the art.

The combinations of active components I and II according to the present invention have useful contact action and systemic and long-lasting action in the control of seed-borne and soil-borne plant diseases. Microorganisms in the seed are destroyed and plants in the process of developing are protected from attack by soil-borne microorganisms by the combinations according to the invention.

The mixtures according to the invention are effective against phytopathogenic fungi belonging to the following classes: Ascomycetes (e.g. the genera Mycosphaerella, Pyrenophora); Basidiomycetes (e.g. the genera Tilletia, Rhizoctonia); *Fungi imperfecti* (e.g. the genera Fusarium, Septoria, Phoma, Alternaria). The combinations according to the invention are especially effective in seed treatment (fruit, tubers, grains), activity against *Fusarium virale* on wheat being especially pronounced. They are, however, also suitable for direct treatment of the soil or other plant parts. They are well tolerated by plants and are ecologically non-harmful.

In practice, the mixture according to the invention is normally used together with the adjuvants customarily employed in the art of formulation. The active components of formulae I and II are formulated in known manner, e.g. to emulsifiable concentrates, coatable pastes, directly sprayable or dilutable solutions, dilute emulsions, wettable powders, soluble powders, dusts, granulates, and also encapsulations in, e.g., polymer substances. The methods of application, such as spraying, atomising, dusting, scattering, coating or pouring, and the form of the composition are in accordance with the intended objectives and the prevailing circumstances. Advantageous rates of application are generally from 0.0005 to a maximum of 0.5 kg, especially from 0.001 to 0.01 kg of each of active ingredients I and II per 100 kg of material to be protected. The application conditions depend to a very considerable extent, however, on the nature (size of the surface, consistency, moisture content) of the material and on environmental factors.

Within the scope of the present invention, stored and stock materials and especially seed are to be understood as being natural plant and/or animal substances and products of their further processing, for example the following plants and their parts, (stems, leaves, tubers, seed, fruit, grains) which have been taken from the natural life cycle and which are present in the freshly harvested state or in further processed form (pre-dried, moistened, pulverised, ground, roasted, etc.).

Target crops to be protected within the scope of this invention comprise e.g. the following species of plants: cereals: (wheat, barley, rye, oats, rice, sorghum, maize and related crops); beet: (sugar beet and fodder beet); leguminous plants: (beans, lentils, soybeans, peas); oil plants: (rape, mustard, poppy, sunflowers); cucumber plants: (marrows, cucumbers, melons); fibre plants: (cotton, flax); vegetables: (lettuce, cabbages, spinach, carrots, onions, tomatoes, potatoes, paprika); ornamentals: (tulips, daffodils, dahlias, chrysanthemums and other flowers) and spice plants and their seeds.

A preferred method of applying the mixture according to the invention consists in spraying or wetting the plant material with a liquid formulation or in mixing the plant material with a solid formulation of the active ingredient. The described method of preservation forms part of the present invention.

The compounds of formulae I and II are used according to the invention in the form of compositions and may be employed optionally together with further carriers, surfactants or other application-promoting adjuvants customarily used in the art of formulation.

Suitable carriers and adjuvants can be solid or liquid and correspond to the substances expediently employed in formulation technology, e.g. natural or regenerated mineral substances, solvents, dispersants, wetting agents, tackifiers, thickeners, binders or fertilizers. Phospholipids are especially advantageous adjuvants.

A preferred method of applying a mixture of compounds of formulae I and II, or an (agro)chemical composition which contains these compounds, is foliar application. The number of applications and the rate of application depend on the risk of infestation by the corresponding pathogen (species of fungus). However, the active ingredient mixture can also penetrate the plant through the roots via the soil (systemic action) by impregnating the locus of the plant with a liquid formulation, or by applying the compounds in solid form to the soil, e.g. in granular form (soil application). The mixture of the compounds of formulae I and II can, according to an especially preferred method, be applied to seed grains, tubers, fruit or other plant material to be protected (coating) either by impregnating the material with a liquid formulation of the active ingredients or by coating it with a solid formulation. In special cases, further types of application are also possible, for example selective treatment of the plant stems or buds.

The compounds of formulae I and II are used in unmodified form or, preferably, together with the adjuvants conventionally employed in the art of formulation, and are therefore formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application in the case of field treatment are normally from 5 g to 5 kg of active ingredient (a.i.) of formulae I and II per hectare, preferably from 10 g to 2 kg a.i./ha, most preferably from 20 g to 600 g a.i./ha.

The formulations, i.e. the compositions, preparations or mixtures containing the compound (active ingredient) of formulae I and II and, where appropriate, a solid or liquid adjuvant, are prepared in known manner, e.g. by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their esters, such as ethylene glycol monomethyl ether, ketones such as cyclohexanone, strongly polar solvents such as N-methyl-2-pyrrolidone, dimethyl sulfoxide or dimethylformamide, as well as vegetable oils or epoxidised vegetable oils, or soybean oil; or water.

The solid carriers used e.g. for dusts and dispersible powders, are calcite, talcum, kaolin, montmorillonite or attapulgite, highly dispersed silicic acid or absorbent polymers. Suitable granulated adsorptive carriers are pumice, broken brick, sepiolite or bentonite; and suitable nonsorbent carriers are, for example, calcite or dolomite.

Depending on the nature of the compounds of formulae I and II to be formulated, suitable surface-active compounds are non-ionic, cationic and/or anionic surfactants having good emulsifying, dispersing and wetting properties. The term "surfactants" will also be understood as comprising mixtures of surfactants.

The surfactants customarily employed in the art of formulation have appeared, inter alia, in the following publications:

"Mc Cutcheon's Detergents and Emulsifiers Annual" MC Publishing Corp., Ridgewood N.J., 1980

Sisley and Wood, "Encyclopedia of Surface Active Agents", Chemical Publishing Co. Inc., New York, 1980.

Especially advantageous application-promoting adjuvants are also natural or synthetic phospholipids from the series of the cephalins and lecithins, e.g. phosphatidylethanolamine, phosphatidylserine, phosphatidylglycerol and lysolecithin.

The agrochemical compositions usually contain 0.1 to 99%, preferably 0.1 to 95%, of a compound of formula I, 99.9 to 1%, preferably 99.9 to 5%, of a solid or liquid adjuvant, and 0 to 25%, preferably 0.1 to 25%, of a surfactant.

Whereas commercial products will preferably be formulated as concentrates, the end user will normally employ dilute formulations.

Such (agro)chemical compositions form part of the present invention.

The following Examples serve to illustrate the invention, "active ingredient" denoting a mixture of "fenpiclonil" I and compound II in a specific ratio.

| Wettable powders | (a) | (b) | (c) |
| --- | --- | --- | --- |
| active ingredient (I:II = 10:1, 5:2, 1:3) | 25% | 50% | 75% |
| sodium lignosulfonate | 5% | 5% | — |
| sodium laurylsulfate | 3% | — | 5% |
| sodium diisobutylnaphthalenesulfonate | — | 6% | 10% |
| octylphenol polyethylene glycol ether (7-8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is thoroughly ground in a suitable mill, affording wettable powders which can be diluted with water to give suspensions of the desired concentration.

| Emulsifiable concentrate | |
| --- | --- |
| active ingredient (I:II = 1:20) | 10% |
| octylphenol polyethylene glycol ether (4-5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| Dusts | (a) | (b) |
| --- | --- | --- |
| active ingredient (I:II = 2:3 and 1:1) | 5% | 8% |
| talcum | 95% | — |
| kaolin | — | 92% |

Ready-for-use dusts are obtained by mixing the active ingredient with the carrier and grinding the mixture in a suitable mill.

| Extruder granulate | |
| --- | --- |
| active ingredient (I:II = 20:1) | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| Coated granulate | |
| --- | --- |
| active ingredient (I:II = 3:2) | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

BIOLOGICAL EXAMPLES

A synergistic effect has been achieved with fungicides whenever the fungicidal action of the combination of active ingredients is greater than the sum of the action of the active ingredients applied individually.

The expected action E for a given combination of active ingredients, for example of two fungicides, obeys the so-called COLBY formula and can be calculated as follows (COLBY, L. R., "Calculating synergistic and antagonistic responses of herbicide combination". Weeds 15, pages 20-22.2) (LIMPEL et al., 1062 "Weeds control by . . . certain combinations". Proc. NEWCL, Vol. 16, pp. 48-53):

(g a.i./hl=gram of active ingredient per hectoliter of spray mixture)
$X = \%$ action of fungicide I at p g a.i./ha
$Y = \%$ action of fungicide II at q g a.i./ha
$E =$ expected action of fungicides I+II at a rate of application of p+q g a.i./ha (additive action)
then according to Colby:

$$E = X + Y - \frac{X \cdot Y}{100}$$

If the action actually observed (0) is greater than the calculated action, then the action of the combination is greater than additive, i.e. there is a synergistic effect.

Fungicidal activity against seed-borne *Septoria nodorum* on winter wheat

The wheat seed ("Moleson" variety) infected with *Septoria nodorum* is harvested from the field. The malt-agar test shows that the seed is 53% infected. The seed is treated with mixtures of the active ingredients as shown in the following Table. To ensure uniform treatment, the active components are first dispersed in water and then sprayed onto the seed which is on a rotating bed. This procedure corresponds to standard conventional practice.

The treated seed is sown in arable soil. The arable soil is placed in dishes of the following size: depth 11 cm, length 40 cm, width 30 cm. 100 grains are used in each dish and three parallel tests are carried out for each combination.

The efficacy of the individual products is assessed using the method disclosed by Holmes and Colhoun (S. J. I. Holmes and J. Colhoun: "A method for assessing the efficacy of seed infectants for the control of seed-borne *Septoria nodorum* on wheat". Annals of Applied Biology 75 pp. 225-232, 1973).

After sowing, the dishes are kept for two weeks at from 8° to 10° C. with the exclusion of light and are then placed in a greenhouse and kept there at 20° C. for a further two weeks. The seedlings are then taken from the soil and washed. The degree of damage to these plants is compared with the degree of fungus attack in the untreated control plants.

TABLE

| treatment no. | g active ingredient 100 kg seed | | fungus attack (%) | action E (calculated) (%) (COLBY) | action O (found) (%) |
|---|---|---|---|---|---|
| | component I | component II | | | |
| 1. comparison | — | — | 100 | — | — |
| 2. | 1 | — | 88 | — | 12 |
| 3. | 2 | — | 87 | — | 13 |
| 4. | 5 | — | 65 | — | 35 |
| 5. | 10 | — | 54 | — | 46 |
| 6. | — | 1 | 60 | — | 40 |
| 7. | — | 2 | 44 | — | 56 |
| 8. | — | 5 | 25 | — | 75 |
| 9. | — | 10 | 17 | — | 83 |
| 10. | 1 | 1 | 44 | 47 | 56 |
| 11. | 1 | 2 | 32 | 62 | 68 |
| 12. | 1 | 5 | 20 | 78 | 80 |
| 13. | 1 | 10 | 13 | 85 | 87 |
| 14. | 2 | 1 | 41 | 48 | 59 |
| 15. | 2 | 2 | 28 | 62 | 72 |
| 16. | 5 | 1 | 36 | 60 | 64 |
| 17. | 5 | 2 | 21 | 71 | 79 |
| 18. | 10 | 1 | 21 | 68 | 79 |
| 19. | 10 | 2 | 19 | 77 | 81 |
| 20. | 10 | 5 | 10 | 87 | 90 |
| 21. | 10 | 10 | 5 | 91 | 95 |

As can be seen from the Table, treatments nos. 10–21, in which components I and II were used in a wide variety of ratios, exhibit an enhanced, i.e. synergistic, activity.

Similarly enhanced, i.e. synergistic, activity is exhibited against snow mould (*Gerlachia nivalis*) on wheat, barley and rye, against *Pyrenophora graminea* and *P. teres* on barley, against *Tilletia caries* on wheat, against Ustilago on barley and against other seed-borne and soil-borne pathogens.

What is claimed is:

1. A fungicidal composition for plants containing a synergistic fungicidally effective amount of the mixture of at least two active ingredient components, wherein one component (I) is 3-cyano-4-(2,3-dichlorophenyl)-pyrrole of formula I

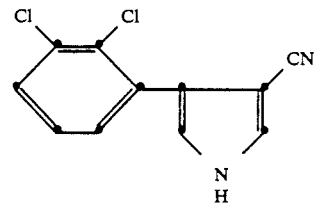
(I)

and the other component (II) is 1-(1H-1,2,4-triazol-1-yl)-2-methoxy-2-[4-(4-chlorophenoxy)-2-chlorophenyl]-butane of formula II

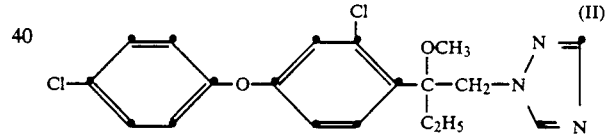
(II)

or a salt thereof, together with a carrier, wherein the weight ratio of I:II is 20:1 to 1:20.

2. The composition according to claim 1, wherein the weight ratio of I:II is 5:1 to 1:5.

3. A method of controlling or preventing plant fungal diseases, which comprises treating the plant locus which is already infected, or is liable to be infected, in any order or simultaneously with a synergistic fungicidally effective amount of the composition of claim 1.

4. The method according to claim 3, which comprises treating the seed.

* * * * *